United States Patent [19]

Gao et al.

[11] Patent Number: 5,516,943
[45] Date of Patent: May 14, 1996

[54] PROCESS FOR PREPARING CYCLIC CIS-1-AMINO-2-ALKANOLS

[75] Inventors: Yun Gao, Framingham; Yaping Hong; Xiaoyi Nie, both of Worcester; Roger P. Bakale, Shrewsbury; Richard R. Feinberg, Bristol; Charles M. Zepp, Berlin, all of Mass.

[73] Assignee: Sepracor, Inc., Marlborough, Mass.

[21] Appl. No.: 121,340

[22] Filed: Sep. 14, 1993

[51] Int. Cl.$^6$ ................................................. C07C 209/58
[52] U.S. Cl. ........................... 564/444; 564/1; 564/414; 564/424; 564/428
[58] Field of Search ................................. 564/414, 424, 564/444, 1, 428

[56] References Cited

U.S. PATENT DOCUMENTS 5,043,341  8/1991  Cohen et al. ............................ 514/288

FOREIGN PATENT DOCUMENTS 482797  4/1992  European Pat. Off. .

OTHER PUBLICATIONS

Tucker et al. "A Series of Potent HIV–1 Protease Inhibitors Containing a . . . " *J. Med. Chem.* 35, 2525–33 (1992).
Young et al. "HIV–1 Protease Inhibitors Based on Hydroxyethylene . . . " *J. Med. Chem.* 35, 1702–1709 (1992).
Thompson et al. "Synthesis and Antiviral Activity of a Series of HIV–1 . . . " *J. Med. Chem.* 35, 1685–1701 (1992).
Armstrong et al. "Stereocontrolled Addition of Chiral, Non-–Racemic Amide . . . " *Tetrahedron Letters* 33, 6599–6602 (1992).
Lutz et al. "Further Studies on the Stability of β–Hydroxyethylamines . . . " *J. Am. Chem. Soc.* 73, 1639–1641 (1951).
Jacobsen et al. "Highly Enantioselective Epoxidation Catalysts Derived from 1,2–Diaminocyclohexane" *J. Am. Chem. Soc.* 113, 7063–64 (1991).
Askin et al. "Highly Diastereoselective Alkylations of Chiral Amide" *J. Org. Chem.* 57, 2771–2773 (1992).
Lyle et al. "Benzocycloalkyl amines as Novel C–Termini for . . . " *J. Med. Chem.* 34, 1228–1230 (1991).
McCasland et al. "Stereochemistry of Aminocyclanols. Synthesis of . . . " *J. Amn. Chem. Soc.* 72, 2190–2195 (1950).
Bannard et al. "Reaction of trans–2–Acylaminocyclanols with Thionyl Chloride" *Can. J. Chem.* 49, 2064–2072 (1970).
McCarthy et al. "Stereospecific Synthesis of the Four Diastereomeric" *J. Org. Chem.* 50, 3095–3103 (1985).
Ghosh et al. "Stereoselective Reduction of α–Hydroxy Oxime Ethers . . . " *Tetrahedron Letters* 32, 711–714 (1991).
Hassner et al. "Addition of Iodine Isocyanate to Olefins . . . " *J. Org. Chem.* 32, 540–549 (1967).
Johnson et al. "Ring Closure of the 2–Benzoylaminocyclohexanols . . . " *J. Am. Chem. Soc.* 72, 2187–2190 (1950).
Winstein et al. "The Role of Neighboring Groups in Replacement Reactions . . . " *J. Am. Chem. Soc.* 72, 4669–4677 (1950).
Drefahl et al. "Aminoalkohole, I: cis–und tran–DL–1–amino–2–hydroxy–tetralin und . . . " *Chemische Berichte* 91, 266–70 (1958).
Braun et al. "Alkamine und Äther–basen der Tetralin–und Hydrinden–Reihe" *Chemische Berichte* 73, 3052–59 (1930).
Karrer, Organic Chemistry 3d English Edition, pp. 100–105 (1947).

*Primary Examiner*—Richard L. Raymond
*Assistant Examiner*—Scott C. Rand
*Attorney, Agent, or Firm*—Heslin & Rothenberg

[57] ABSTRACT

A two-step process for the conversion of a trans-1-amino-2-hydroxycycloalkane stereoselectively to a cis-1-amino-2-hydroxycycloalkane is disclosed. The novel step, a one-step hydrolysis with formal inversion, can be used to convert an amide of a trans-1-amino-2-hydroxycycloalkane to a cis-1-amino-2-hydroxycycloalkane. Methods for obtaining the trans-1-amino-2-hydroxycycloalkanes and their amides from alkenes are also disclosed. A preferred process converts indene to cis-1-amino-2-indanol.

24 Claims, No Drawings

PROCESS FOR PREPARING CYCLIC CIS-1-AMINO-2-ALKANOLS

FIELD OF THE INVENTION

The invention relates to a process for preparing cyclic cis-1-amino-2-alkanols from cyclic trans-1-amino-2-alkanols or the amides Of trans-1-amino-2-alkanols.

BACKGROUND OF THE INVENTION

Cyclic cis-1-amino-2-alkanols are useful as chiral auxiliaries and as intermediates in the synthesis of pharmaceuticals. For example, optically pure cis- (1S, 2R) -1-amino-2-indanol (I)

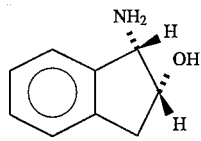

has been used as an intermediate in the preparation of HIV-1 protease inhibitors for anti-viral and anti-AIDS therapy (T. J. Tucker et al. J. Med. Chem. 35, 2525–2533 (1992); S. D. Young et al. J. Med. Chem. 35, 1702–1709 (1992); W. J. Thompson et al. J. Med. Chem. 35, 1685–1702 (1992)). In addition, optically pure cis-1-amino-2-indanol has been used as a chiral auxiliary for the asymmetric addition of amide homoenolates to aldehydes (J. D. Armstrong, III, et al. *Tetrahedron Lett.* 44, 6599–6602 (1992)). Cyclic cis-1-amino-2-alkanols are commonly prepared from the corresponding trans-1-aminoalkanols, which are synthetically much more accessible. For example, Lutz and Wayland have described the preparation of racemic cis-1-amino-2-indanol from racemic trans-1-amino-2-indanol in three steps (R. E. Lutz and R. L. Wayland, Jr., *J. Am. Chem. soc.* 73, 1639–1641 (1951)). Their synthesis is a particular application of what appears to be the most popular method for converting trans aminoalcohols to cis aminoalcohols. It involves the synthesis of an oxazoline by the treatment of the amide with thionyl chloride. The oxazoline is isolated, usually by crystallization for the purpose of purification, and subsequently hydrolyzed, theoretically via an esterammonium salt, to the cis aminoalcohol.

Optically pure cis-(1S,2R)-1-amino-2-indanol has also been obtained by the resolution of the corresponding L-phenylalanine amide diastereomers by chromatographic separation, followed by cleavage of the amide with sodium in ethanol (W. J. Thompson et al. *J. Med. Chem.* 35, 1685–1701 (1992)).

These and other known processes for the preparation of cyclic cis-1-amino-2-alkanols often involve lengthy synthetic transformations and usually provide the desired product in low overall yield. Resolution procedures for obtaining optically pure cis-(1S,2R)-1-amino-2-indanol are notoriously inefficient. A practical preparation of cyclic cis-1-amino-2-alkanols, particularly of optically pure cis-1-amino-2-indanol, would be highly desirable. It is, therefore, an object of the present invention to provide a process for the preparation of cyclic cis-1-amino-2-alkanols from the corresponding cyclic trans-1-amino-2-alkanols or their amides. It is a particular object of the present invention to prepare cis-1-amino-2-indanol from trans-1-amino-2-indanol in good yield and with a minimum of synthetic manipulations. It is also an object of the present invention to prepare optically pure cis-1-amino-2-alkanols such as cis-(1S,2R)-1-amino-indanol, from the corresponding partially resolved or optically pure trans-1-amino-2-alkanols in good yield and with minimum synthetic transformations.

SUMMARY OF THE INVENTION

The objects of the present invention are provided by a process for the preparation of a racemic or optically pure cyclic cis-1-amino-2alkanol from the corresponding trans-1-amino-2alkanol or amide of the trans 1-amino-2-alkanol.

In one aspect the invention relates to a process for the stereospecific conversion of a trans-1-amino2-hydroxycyclopentane to the corresponding cis-1- amino-2-amino-2-hydroxycyclopentane comprising:

(a) reacting a trans-1-amino-2-hydroxycyclopentane with an acylating agent to produce an amide; and (b) treating the amide with an aqueous solution of a strong acid to cleave the amide and effect inversion of the carbon bearing the hydroxyl function to produce a cis-1-amino-2-hydroxycyclopentane.

In another aspect the invention relates to a process for the stereospecific conversion of an amide of a trans-1-amino-2-hydroxycyclopentane to the corresponding cis-1-amino-2-hydroxycyclopentane by treating the amide of the trans-1-amino-2-hydroxycyclopentane with a solution of a strong acid to cleave the amide and effect inversion of the carbon bearing the hydroxyl function to produce a cis-1-amino-2-hydroxycyclopentane.

Preferred strong acids include hydrochloric, sulfuric, methanesulfonic and triflic acids. The amide is preferably an acetamide, propanamide, butanamide, benzamide, chlorobenzamide, nitrobenzamide, anisamide or toluamide, most preferably the amide is a benzamide.

In one embodiment the trans-1-amino-2-hydroxycyclopentane may be trans-1-amino-2-indanol. If the trans-1-amino-2-hydroxycyclopentane is trans-(1S,2S)-amino- 2-indanol, it is converted to cis-(1S, 2R)-1-amino-2-indanol; if the trans-1-amino-2-hydroxycyclopentane is trans-(1R,2R)-1-amino-2-indanol, it is converted to cis-(1R,2S)-1-amino-2-indanol. When the amino alkanol is partially resolved trans-1-amino-2-indanol and the amide is a benzamide, an additional step of recrystallizing the benzamide produces substantially optically pure trans-1-benzamido-2-indanol.

In a further aspect, the invention relates to a process for producing a cis-1-amino-2-indanol from an indene comprising the steps of:

(a) oxidizing the indene to produce an indene oxide;

(b) converting the indene oxide to an amide of a trans-1-amino-2-indanol; and (c) treating the amide of the trans-1-amino-2-indanol with a solution of a strong acid to cleave the amide and effect inversion of the carbon bearing the hydroxyl function to produce a cis-1-amino-2-indanol.

The trans amide can be made from the epoxide either (1) by treating the indene oxide with ammonia or a primary amine to produce a trans-1-amino-2-indanol and reacting the trans-1-amino-2-indanol with an acylating agent, or (2) by treating the epoxide with an amide anion to produce the trans hydroxy amide directly. In one embodiment the indene is oxidized with aqueous hypochlorite in the presence of a chiral salen catalyst to produce a partially resolved epoxide, which is converted to the partially resolved trans-1-amino-2-indanol by treating with ammonia or a primary amine followed by acylating with benzoyl chloride. The resulting benzamide is recrystallized to yield substantially optically pure trans-1-benzamido-2-indanol. In two preferred embodiments, the cis-1-amino-2-indanols are (1S,2R)-1- amino-2-indanol and (1R,2S)-1-amino-2-indanol, produced by oxidation of indene in the presence of an R,R or S,S-salen catalyst respectively.

In a further aspect the invention relates to a process for producing a compound of formula II

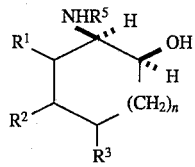

comprising the steps of
(a) reacting a trans aminoalcohol of formula III

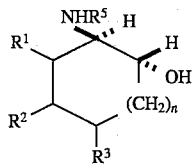

with an acylating agent of formula $R^4CO\text{-}X$ to produce an amide of formula IV

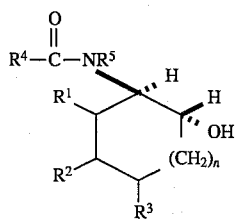

and
(b) treating the amide with an aqueous solution of a strong acid, wherein
   $R^1$ is hydrogen, alkyl, aryl or substituted aryl;
   $R^2$ is hydrogen, alkyl, aryl or substituted aryl;
   $R^3$ is hydrogen, alkyl, aryl or substituted aryl;
   $R^4$ is hydrogen, alkyl, aryl or substituted aryl;
   $R^5$ is hydrogen, alkyl, aryl or substituted aryl; or
   $R^1$ and $R^2$ together form a 1,2-fused alicyclic, aryl or substituted aryl residue; n is zero or an integer from one to there, preferably zero or one; and X is an activating group for the acylation of amines.

When $R^1$ and $R^2$ together form a 1,2-fused aryl or substituted aryl residue and $R^3$ and $R^5$ are hydrogen, a preferred process may comprise the additional steps of oxidizing an indene to an indene oxide and opening the indene oxide with ammonia to produce the trans-1-amino-2-indanol V.

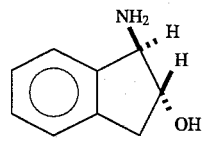

In a further aspect the invention relates to a process for the stereospecific conversion of a trans-1-amino-2-hydroxycyclohexane to the corresponding cis-1-amino-2-hydroxycyclohexane comprising:
(a) reacting a trans-1-amino-2-hydroxycyclohexane with an acylating agent to produce an amide; and
(b) treating the amide with an aqueous solution of a strong acid to cleave the amide and effect inversion of the carbon bearing the hydroxyl function to produce a cis-1-amino-2-hydroxycyclohexane.

A preferred trans-1-amino-2-hydroxycyclohexane is trans-1-amino-5,6-benzocyclohexan-2-ol.

In a further aspect the invention relates to a process for the stereospecific conversion of an amide of a trans-1-amino-2-hydroxycyclohexane to the corresponding cis-1-amino-2-hydroxycyclohexane comprising treating the amide with an aqueous solution of a strong acid to cleave the amide and effect inversion of the carbon bearing the hydroxyl function to produce a cis-1-amino-2-hydroxycyclohexane.

DETAILED DESCRIPTION OF THE INVENTION

The central process of the invention comprises reacting an amide of a trans-1-amino-2-cycloalkanol with a strong acid to provide a cis-1-amino-2-cycloalkanol. The result of this process is most unexpected; it would be anticipated that the treatment of an amide with aqueous acid would do no more than hydrolyze the amide, i.e. produce a trans amidoalcohol from a trans aminoalcohol.

The process of the invention can further comprise reaction of a trans-1-amino-2-cycloalkanol with an acylating agent such as an acyl halide or a carboxylic acid anhydride to give the corresponding carboxylic amide, followed by treatment of the amide under strong acid conditions to give the desired cis-1-amino-2-alkanol in good yield and in only two steps. The present invention is particularly suitable for the preparation of a racemic or optically pure cis-1-amino-2-indanol such as cis-(1S,2R)-1-amino-2-indanol. According to the present invention, an optically pure cis-1-amino-2-indanol can be prepared from an optically pure amide intermediate. The optically pure amide may be obtained by acylation of an optically pure amine or by recrystallization of the benzamide of partially resolved trans-1-amino-2-indanol.

The graphic representations of racemic, ambiscalemic and scalemic or enantiomerically pure compounds used herein are taken from Maehr *J. Chem. Ed.* 62, 114–120 (1985): solid and broken wedges are used to denote the absolute configuration of a chiral element; wedge outlines and dotted or broken lines denote enantiomerically pure compounds of indeterminate absolute configuration; wavy lines indicate disavowal of any stereochemical implication which the bond it represents could generate; and solid and broken bold lines, as in II, III and IV are geometric descriptors indicating the relative configuration shown but denoting racemic character.

The present invention can be more easily understood when reference is made to general Schemes A and B for the preparation of cyclic cis-1-amino-2-alkanols.

Scheme A cyclopentanes:

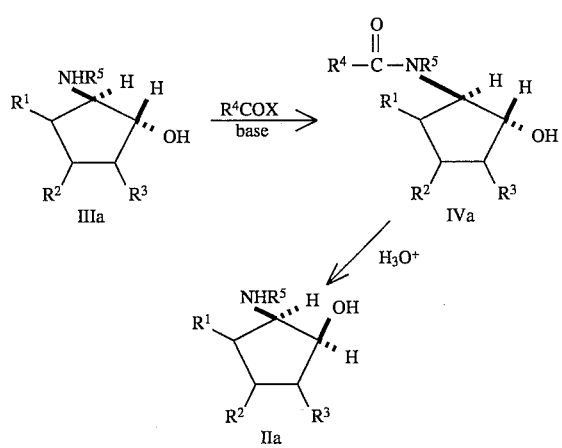

Scheme B and similarly for cyclohexanes:

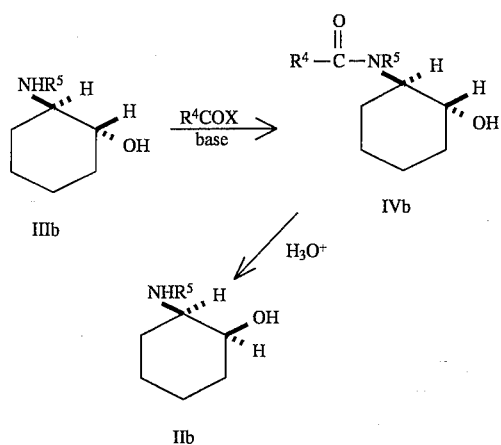

trans-1-amino-2-alkanol (III) is reacted with an equal molar or slight excess of an acylating agent to give the amide (II) under basic conditions. The amide is then treated under aqueous conditions in the presence of a strong acid. After basification with bases such as NaOH or KOH, the cis-1-amino-2-alkanol (III) is obtained by simple extraction with an organic solvent such as methylene chloride.

If the starting material (trans aminoalcohol) is racemic, racemic cis aminoalcohol will be produced, as illustrated in Schemes A and B. If the starting material is optically pure trans aminoalcohol, the product will be optically pure (e.g. Scheme A'):

Scheme A'

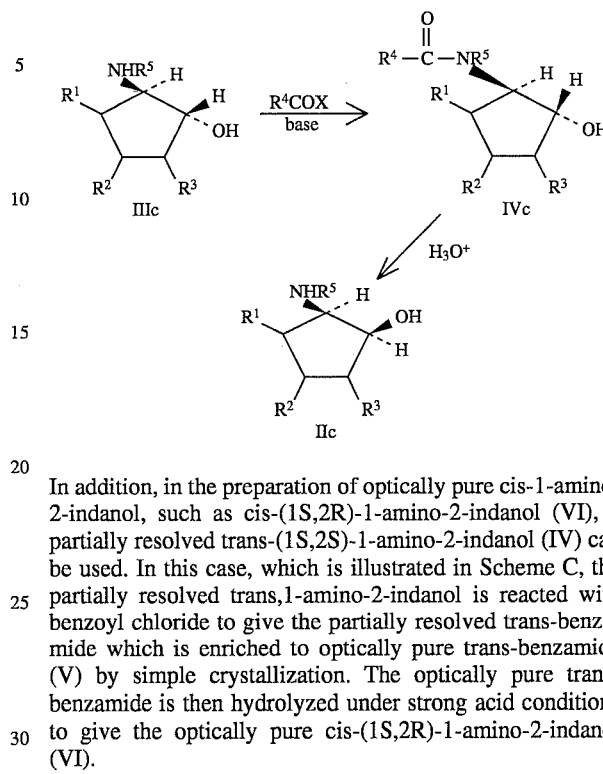

In addition, in the preparation of optically pure cis-1-amino-2-indanol, such as cis-(1S,2R)-1-amino-2-indanol (VI), a partially resolved trans-(1S,2S)-1-amino-2-indanol (IV) can be used. In this case, which is illustrated in Scheme C, the partially resolved trans,1-amino-2-indanol is reacted with benzoyl chloride to give the partially resolved trans-benzamide which is enriched to optically pure trans-benzamide (V) by simple crystallization. The optically pure trans-benzamide is then hydrolyzed under strong acid conditions to give the optically pure cis-(1S,2R)-1-amino-2-indanol (VI).

Scheme C

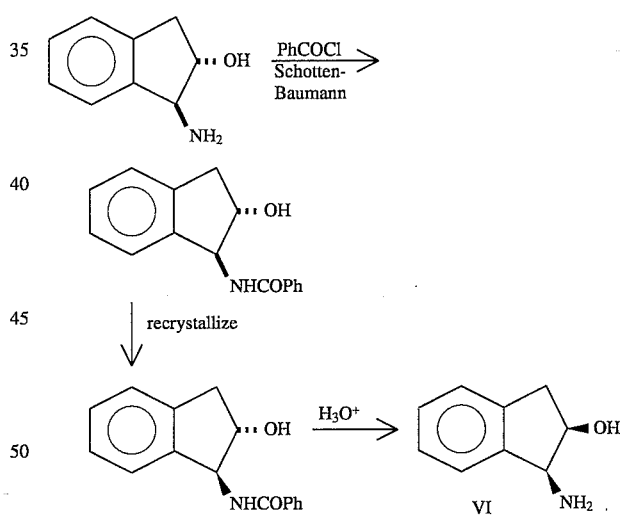

The complete resolution of partially resolved trans benzamide is effective in this case because the enantiomers form a conglomerate or racemic mixture (as opposed to a racemic compound or racemate), and the solubility of the racemic mixture is higher than the solubility of either enantiomer. An enantiomeric excess (ee) of a few percent of either enantiomer in the trans benzamide will suffice to effect resolution. Mixtures having 80% ee are readily purified to >99% ee in one recrystallization. The term "substantially optically pure" refers to compositions containing >98% ee of a single enantiomer.

As will be understood by persons of skill in the art, the leaving group X in the acylating agent admits of wide variation. Any acylating agent capable of converting an amine to an amide will function in the invention. Thus, the leaving group X can be, for example, a halogen, an activated phenol, an azide, an acyloxy residue (an anhydride) or the like.

The conversion of the trans amide to cis aminoalkanol exhibits high stereoselectivity only when the acid is a strong acid in fairly high concentration. Thus, for example, hydrochloric and sulfuric acids are particularly well suited. Hydrochloric acid should be at least 6 normal; sulfuric acid should be greater than 30%. When concentrations of acid lower than these are used, the hydrolysis still exhibits some stereoselectivity, but the selectivity is not as high as it is in more concentrated solutions. Preferred strong acids are aqueous HCl in the range 343 of 6N–12N or aqueous $H_2SO_4$ in the range of 30–80 wt %, preferably in the range of 50–80 wt %. Methanesulfonic acid, triflic acid (trifluoromethanesulfonic acid), hydrobromic acid and similar strong acids may also be considered; their effective concentration is a matter of simple experimentation which is within the skill of the ordinary artisan. Strong acids are defined as those acids which are completely dissociated in 0.1M aqueous solution.

A temperature in the range of 80°–120° C. is optimal. The reaction should be carried out for sufficient time to allow complete inversion and hydrolysis, usually a period of 3–20 hr.

In order to isolate the basic cis-1-amino-2-alkanol, the reaction mixture is usually basified with a base such as NaOH or KOH to above pH 9, preferably to pH 11–13, and the cis-1-amino-2-alkanol is extracted from the basic aqueous mixture with an inert organic solvent, such as methylene chloride, 1,2-dichloroethane, or a water insoluble alcohol such as n-butanol. After removal of the solvent and further purification using methods standard in organic synthesis, such as distillation and crystallization, the cis-1-amino-2-alkanol is obtained. Alternatively, the cis-1-amino-2-alkanol can be isolated from the reaction by passing the reaction mixture through a basic anion-exchange resin followed by simple isolation.

In the reaction of the trans-1-amino-2-alkanol with an acyl halide or acid anhydride, the acyl halide may be, for example, benzoyl chloride, acetyl chloride, benzoyl bromide, or toluoyl chloride. The acid anhydride may be, for example, benzoic anhydride, acetic anhydride or butyric anhydride. The reaction can be carried out in the presence of an inorganic base such as NaOH or KOH in an inert organic solvent and water mixture such as acetone-water or tetrahydrofuran (THF)-water under standard Schotten-Baumann conditions, or it may be carried out in the presence of an organic base such as triethylamine or 4-dimethylaminopyridine in an inert organic solvent or solvent mixture according to organic procedures (J. March *Advanced Organic Chemistry*, 3rd Ed., 370–371 (1985)).

Trans-1-amino-2-alkanols are advantageously prepared by the reaction of ammonia or a primary amine, such as methylamine, with the corresponding epoxide or bromohydrin according to literature methods (R. E. Lutz and R. L. Wayland, Jr. *J. Am. Chem. Soc.* 73, 1639–1641 (1951)). Examples of trans-1-amino-2-alkanols are: racemic trans-1-amino-2-indanol, substituted trans-1-amino-2-indanol and trans-1-amino-5,6-benzocyclohexan-2-ol. Optically pure trans-1-amino-2-indanol can be obtained by the resolution of racemic trans-1-amino-2-indanol with an optically pure chiral acid. In a preferred embodiment of the present invention, partially resolved trans-1-amino-2-indanol is obtained by the reaction of ammonia with partially resolved indene oxide which itself can be made by the asymmetric epoxidation of indene by any of a number of procedures known in the art. A particularly effective procedure utilizes sodium hypochlorite [E. N. Jacobsen et al. *J. Am. Chem. Soc.* 113, 7063–7064 (1991) and references therein)]. A preferred catalyst for the chiral oxidation is the salen of

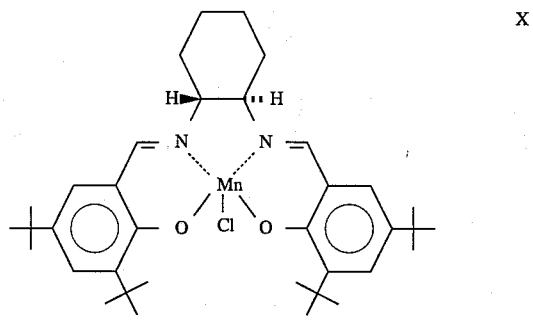

Salens are transition metal complexes of Schiff bases of a salicylaldehyde and a chiral amine. The particular salen shown is of the R,R configuration and provides 80–85% ee of the (1R,2S)-epoxide which can be carried on to the predominantly (S,S)-transaminoalcohol. Use of the S,S-salen provides the corresponding (1S,2R)-epoxide in similar fashion. The overall conversion is shown in Scheme D.

Scheme D

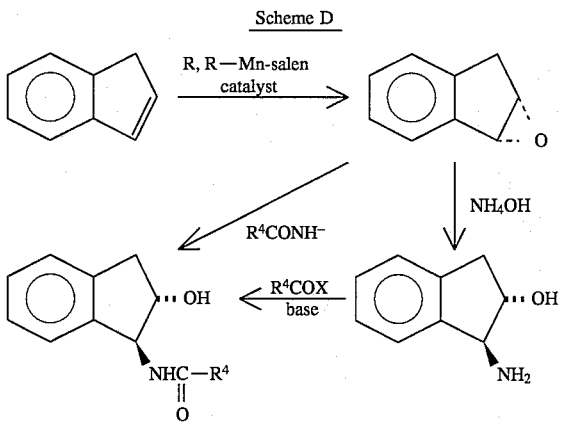

The benzamide of partially resolved trans-1-amino-2-indanol can be conveniently prepared from the partially resolved indene oxide by reaction of the indene oxide with aqueous ammonia followed by reaction with benzoyl chloride in the presence of a base such as NaOH using the Schotten-Baumann procedure without isolation of the trans-1-amino-2-indanol intermediate. Partially resolved trans-benzamide of trans-1-amino-2-indanol can be enriched to optically pure trans-benzamide by crystallization from an organic solvent such as ethanol (EtOH) or (MeOH) or solvent mixture such as MeOH-dimethylformamide (DMF) or EtOH-DMF.

An alternative synthesis of the amides of trans-1-amino-2-hydroxycycloalkanes from epoxides, such as indene oxide, can be envisioned wherein the epoxide is opened with an anion, or anion-equivalent, of an amide to create the amide directly from the epoxide. In this case the overall conversion of indene to cis-1-amino-2-indanol can be accomplished in three steps.

In order to fully illustrate the nature of the invention and the manner of practicing the same, the following examples are presented:

EXAMPLE 1

A 5-L three neck Morton-type flask equipped with an overhead stirrer, an addition funnel and a thermometer was charged with 2.5 L of NaOCl (10% aq, 2.0 eq, 4.0 mol). The solution was cooled to ca. 5°–10° C. A solution of (R,R)-Mn-Salen catalyst X (19.1 g, 0.015 eq, 0.03 mol) in 150 mL of $CH_2Cl_2$ was added, followed by a solution of indene (260 mL, 1.0 eq, 2.0 mol) in 100 mL of $CH_2Cl_2$ at 5°–10° C. The mixture was stirred vigorously at 5°–10° C. for 4 hr. Heptane (1.4L) and Celite (40 g) were added and the mixture stirred for 40 min without cooling. The mixture was filtered and the flask and the solid cake were washed with 200 mL of heptane.

The combined filtrates containing partially resolved indene oxide were concentrated to ca. 400 mL and the concentrate treated with 1.4 L of aqueous ammonia (28% aq.) in 600 mL of MeOH in the presence 20 g of Celite at 25°–30° C. for 15 hr. The MeOH and excess of ammonia were removed by distillation over a period of 4–5 hr until the pot temperature reached 90° C. Water (550 mL) was added and the hot mixture filtered. The flask and solid filter cake were washed with ca. 400 mL of hot water. The combined filtrates were placed under vacuum for 40 min to remove remaining ammonia and transferred to a 5-L Morton-type flask.

The above solution, containing partially resolved trans-(1S,2S)-1-amino-2-indanol, was cooled to ca. 15°–25° C. and NaOH (50% aq., 192 g) and acetone (800 mL) were added. Benzoyl chloride (1.2 eq, 2.4 mol, 280 mL) was added at 15°–25° C. over 1 hr and the resulting slurry stirred at 20°–25° C. for 2 hr. The mixture was filtered and the solid washed with 400 mL of acetone-water (1:1, v/v) and recovered as crude trans-benzamide of partially resolved trans-(1S,2S)-1-amino-2-indanol.

The crude benzamide (ca. 464 g) was dissolved in 1125 mL of DMF at 90° C. and MeOH (750 mL) was added at 80°–86° C. over 1 hour to the DMF solution. The solution was slowly cooled to 0°–5° C. over 1.5 h and held at 0°–5° C. for 2 h. The solid was recovered by filtration, washed with 500 mL cold (0°–5° C.) MeOH and dried under vacuum at 40° C. to give optically pure trans-benzamide of trans-(1S,2S)-1-amino-2-indanol as pale yellow crystals (240 g, 47% yield from indene, 99% ee, m.p. 232° C.).

EXAMPLE 2

A mixture of the trans-benzamide (25 mmol, 6.33 g) from Example 1 and 58.3 mL of 6N aqueous HCl was for 14 hr, cooled to room temperature, washed with 20 mL of $CH_2Cl_2$ and neutralized with 50% aq. NaOH (24 mL) to about pH 13. The mixture was extracted with total of 65 mL of $CH_2Cl_2$, decolorized with 0.5 g of active carbon, filtered and concentrated to ca. 20 mL. Heptane (10 mL) was added to the hot $CH_2Cl_2$ solution and the solution was cooled to 0°–5° C. for 3 h. The white crystals were recovered by filtration and dried as cis-(1S,2R)-1-amino-2-indanol (2 45 g, 66% yield 99 5% ee)

EXAMPLE 3

A mixture of the trans-benzamide from Example 1 (25.3 g, 100 mmol) and 196 g of 50% wt of aqueous $H_2SO_4$ was heated at 120°–123° C. for 3 h, cooled to room temperature and washed with 100 mL of $CH_2Cl_2$. The aqueous solution was neutralized with 150 mL of 50% aq. NaOH at below 50° C. Water (300 mL) was added to dissolve inorganic salts ($Na_2SO_4$) and the mixture was extracted with a total of 280 mL of $CH_2Cl_2$ at 28°–32° C. The $CH_2Cl_2$ extracts were decolorized with 2 g of active carbon and filtered through Celite. The filtrate was concentrated to ca. 130 mL and 60 mL of heptane was added at 40° C. over 10 min. The solution was cooled to 0°–5° C. over 3 h and the resulting solid recovered by filtration as cis-(1S,2R)-1-amino-2-indanol [10.8 g, 73% yield, $[\alpha]D^{25} = -65°(C=1.0, CHCl_3)$].

EXAMPLE 4

A mixture of the trans-benzamide from Example 1 (90g, 355 mmol) and 227 g of 80% wt $H_2SO_4$ was heated at 80°–85° C. for 1 h. The mixture was treated with 377 mL of water and heated to 100°–115° C. for 3.5 h. The mixture was cooled to 30°–35° C. and washed with 355 mL of $CH_2Cl_2$. The aqueous solution was then neutralized with 370 g of 50% NaOH at <50° C., and 175 mL water was added to dissolve the inorganic salts ($Na_2SO_4$). The aqueous mixture was extracted with 535 mL of $CH_2Cl_2$ at 30°–35° C., and the $CH_2Cl_2$ extracts decolorized with 4.5 g activated carbon and dried with 7.5 g $MgSO_4$ (anhydrous). The mixture was filtered through Celite and the filter cake washed with 100mL of $CH_2Cl_2$. The combined filtrates were concentrated to ca. 450mL and 215 mL heptane was added at 40° C. over 30 min. The solution was cooled to 0°–5° C. and the resulting solid recovered by filtration affording cis-(1S,2R)-1-amino-2-indanol (45.2 g, 84% >99.5% ee).

EXAMPLE 5

A 10 g mixture of the combined filtrates from example 1 containing partially resolved indene oxide were concentrated to about 6 mL and the concentrate (ca 160 mmol) was treated with 124 g of 40% aqueous methylamine in 60mL of methanol. The mixture was stirred at 25°–30° C. for 20 hours. The methanol and excess methylamine were removed by distillation and the mixture was dissolved in 250 mL water, acidified with 7 mL HCl (12M) to pH=1, and washed with 250 mL of methylene chloride. The aqueous solution was neutralized with 15 mL of 50% NaOH at <50° C. to pH>13 and extracted with 250 mL of methylene chloride. The methylene chloride extract was decolorized with 1.5 g activated carbon, dried with 2.5 g of $MgSO_4$ (anhydrous), filtered through Celite and the filter cake was washed with 100 mL of methylene chloride. The combined filtrate was concentrated to about 75 mL 75 mL heptane was added at 40° C. over 30 min. The solution was cooled to 0°–5° C., and the resulting white solid recovered by filtration. The cake was washed with 50 mL heptane and vacuum dried at 40° C., to afford 4.3 g of trans-(1S,2S)-1-methylamino-2-indanol (35% of theory, 99.4% by HPLC analysis and >99.5%ee, mp=110°–111° C.). Proton and $C^{13}$ NMR were consistent with the proposed structure.

EXAMPLE 6

A solution of 3.0g (18 mmol) of trans-(1S,2S)-1-methylamino-2-indanol of example 5 in 100 mL of water and 40 mL of THF was cooled to 15°–20° C., and 1.76 g (1.2 eq, 21.6 mmol) of 50% NaOH was added dropwise to the stirred solution. Benzoyl chloride (3.1 g, 1.2 eq, 21.6 mmol) was added at 15°–20° C. over 5 min. with stirring. The resulting slurry was cooled to 0°–5° C. and held for 2 hours. The mixture was filtered, and the cake washed with 25 mL water followed by vacuum drying at 40° C., for 5 hours to afford 4.4 g of trans-(1S,2S)-1-benzoylmethylamino-2-indanol (92% of theory, 99.9% HPLC analysis and 99.1%ee, mp=145°–146° C.). Proton and $C^{13}$ NMR were consistent with the proposed structure.

EXAMPLE 7

A mixture of 2.67 g (10 mmol) of the transbenzamide from Example 6 and 6.4 g of 80% wt $H_2SO_4$ was heated at 80°–85° C. for 1.5 hours. The mixture was then treated with 14.9 g water and heated to 100°–115° C. for 5 hours. The mixture was cooled to 30°–35°, washed with 50 mL of methylene chloride, and the aqueous solution neutralized with 50% NaOH to pH =13. The aqueous mixture was extracted with 75 mL of methylene chloride at 30°–35°, the methylene chloride extracts decolorized with 1 g activated carbon and dried with 1.5 g $MgSO_4$ (anhydrous). The mixture was filtered through Celite and the filter cake was washed with 10mL of methylene chloride. The combined filtrate was concentrated to about 15 mL and 15 mL of heptane was added at 40° C. The slurry was cooled to 0°–5° C. and the resulting white solid was recovered by filtration. Vacuum drying at 40° C. afforded 0.86 g of cis-(1S,2R)-1-methylamino-2-indanol (53% of theory). Proton and $C^{13}$ NMR were consistent with the proposed structure.

EXAMPLE 8

A mixture of 24 g (11 mmol) of racemic trans-2-benzamidocyclohexanol and 12 g of 90% $H_2SO_4$ (110 mmol) was stirred at 75°–80° for 6 hours. After the addition of 22 mL of $H_2O$, the mixture was heated under reflux for 15 hours. The mixture was cooled to room temperature and washed with 20mL of methylene chloride. The acidic aqueous phase was separated, treated with 12.6 mL of 50% NaOH solution (240 mmol) at <40° C., 30mL of $H_2O$ was added and the mixture extracted with a total of 60 mL of methylene chloride at 30°–35° C. The combined extracts were dried over anhydrous $Na_2SO_4$ and filtered. The filtrate was concentrated in vacuo to provide crude product containing cis-2-aminocyclohexanol which was isolated and purified by flash chromatography on silica gel with ethyl acetate-hexane (1:1) to provide 792 mg of cis-2-benzamidocyclohexanol (33% of theory). Proton and $C^{13}$ NMR were consistent with the proposed structure.

We claim:

1. A process for the stereospecific conversion of a trans-1-amino-2-hydroxycyclopentane to the corresponding cis-1-amino-2-hydroxycyclopentane comprising:
    (a) reacting said trans-1-amino-2-hydroxycyclopentane with an acylating agent to produce an amide; and
    (b) treating said amide with a solution of a strong acid to cleave the amide and effect inversion of the carbon bearing the hydroxyl function to produce a cis-1-amino-2-hydroxycyclopentane.

2. A process for the stereospecific conversion of an amide of a trans-1-amino-2-hydroxycyclopentane to the corresponding cis-1-amino-2-hydroxycyclopentane comprising treating said amide with a solution of a strong acid to cleave the amide and effect inversion of the carbon bearing the hydroxyl function to produce a cis-1-amino-2-hydroxycyclopentane.

3. A process according to claim 1 or 2 wherein said strong acid is chosen from the group consisting of hydrochloric, sulfuric, methanesulfonic and triflic acids.

4. A process according to claim 1 or 2 wherein said strong acid is selected from the group consisting of 6N to 12N hydrochloric acid and 30 to 80 wt % sulfuric acid.

5. A process according to claim 1 or 2 wherein said amide is chosen from the group consisting of acetamide, propanamide, butanamide, benzamide, chlorobenzamide, nitrobenzamide, anisamide and toluamide.

6. A process according to claim 1 or 2 wherein said trans-1-amino-2-hydroxycyclopentane is trans-1-amino-2indanol and said cis-1-amino-2-hydroxycyclopentane is cis-1-amino-2-indanol.

7. A process according to claim 6 wherein said amide is a benzamide.

8. A process according to claim 7 wherein said benzamide is partially resolved, comprising the additional step of recrystallizing said benzamide, whereby substantially optically pure trans-1-benzamido- 2-indanol is produced.

9. A process according to claim 8 wherein said substantially optically pure trans-1-benzamido-2-indanol is of the 1S,2S configuration and said cis-1-amino- 2-indanol is cis-(1S, 2R)-1-amino-2-indanol.

10. A process according to claim 6 wherein said trans-1-amino-2-indanol is trans-(1S, 2S)-1-amino-2-indanol and said cis-1-amino-2-indanol is cis-(1S, 2R)- 1-amino-2-indanol.

11. A process for producing a cis-1-amino-2-indanol from an indene comprising the steps of:
    (a) oxidizing said indene to produce an indene oxide;
    (b) converting said indene oxide to an amide of a trans-1-amino-2-indanol; and
    (c) treating said amide of a trans-1-amino- 2-indanol with a solution of a strong acid to cleave the amide and effect inversion of the carbon bearing the hydroxyl function to produce a cis-1-amino-2-indanol.

12. A process according to claim 11 wherein said indene is oxidized with aqueous hypochlorite in the presence of a chiral salen catalyst to produce a partially resolved epoxide.

13. A process according to claim 11 for producing a cis-1-amino-2-indanol from an indene comprising the steps of:
    (a) oxidizing said indene to produce an indene oxide;
    (b) treating said indene oxide with ammonia or a primary amine to produce a trans-1-amino-2-indanol;
    (c) reacting said trans-1-amino-2-indanol with an acylating agent to produce an amide; and
    (d) treating said amide with a solution of a strong acid to cleave the amide and effect inversion of the carbon bearing the hydroxyl function to produce a cis-1-amino-2-indanol.

14. A process according to claim 13 wherein acylating agent is chosen from the group consisting of acetic anhydride, acetyl chloride and benzoyl chloride and the resulting benzamide is recrystallized to yield substantially optically pure trans-1-benzamido-2-indanol or trans-1-acetamido-2-indanol.

15. A process according to claim 14 wherein substantially optically pure cis-1-amino-2-indanol is produced.

16. A process according to claim 15 wherein (1S, 2R)-1-amino-2-indanol is produced from indene by oxidizing indene in the presence of a catalyst of formula 17. A process according to claim 15 wherein (1R, 2S)-1-amino-2-indanol is produced from indene by oxidizing indene in the presence of a catalyst of formula

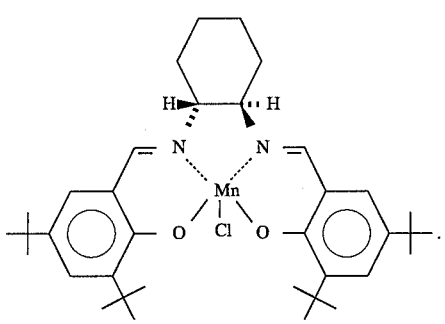

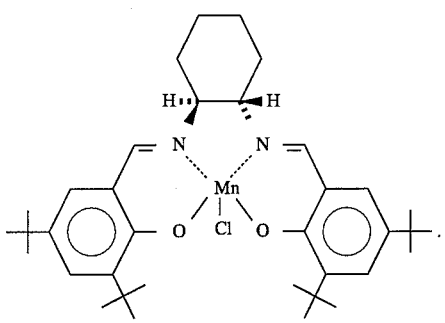

18. A process for producing a compound of formula

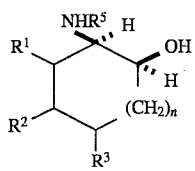

comprising the steps of:
(a) reacting a trans aminoalcohol of formula

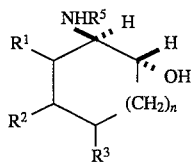

with an acylating agent of formula $R^4CO\text{-}X$ to produce an amide of formula

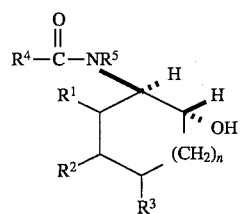

and (b) treating said amide with a solution of a strong acid, wherein $R^1$ is hydrogen, alkyl, aryl or substituted aryl;
$R^2$ is hydrogen, alkyl, aryl or substituted aryl;
$R^3$ is hydrogen, alkyl, aryl or substituted aryl;
$R^4$ is hydrogen, alkyl, aryl or substituted aryl;
$R^5$ is hydrogen, alkyl, aryl or substituted aryl; or
$R^1$ and $R^2$ together form a 1,2-fused alicyclic, aryl or substituted aryl residue;
n is zero or an integer from one to three; and
X is an activating group for the acylation of amines.

19. A process according to claim 18 wherein n is zero or one.

20. A process according to claim 19 for producing

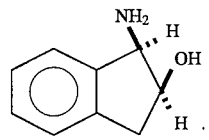

21. A process according to claim 20 comprising the additional steps of oxidizing an indene to an indene oxide and opening said indene oxide with ammonia to provide a trans aminoalcohol of formula

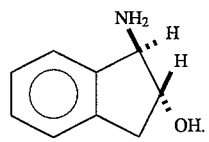

22. A process for the stereospecific conversion of a trans-1-amino-2-hydroxycyclohexane to the corresponding cis-1-amino-2-hydroxycyclohexane comprising:
(a) reacting said trans-1-amino-2-hydroxycyclohexane with an acylating agent to produce an amide; and
(b) treating said amide with an aqueous solution of a strong acid to cleave the amide and effect inversion of the carbon bearing the hydroxyl function to produce a cis-1-amino-2-hydroxycyclohexane.

23. A process according to claim 22 wherein said trans-1-amino-2-hydroxycyclohexane is trans-1-amino-5,6-benzocyclohexan-2ol.

24. A process for the stereospecific conversion of an amide of a trans-1-amino-2-hydroxycyclohexane to the corresponding cis-1-amino-2-hydroxycyclohexane comprising treating said amide with a solution of a strong acid to cleave the amide and effect inversion of the carbon bearing the hydroxyl function to produce a cis-1-amino-2-hydroxycyclohexane.

* * * * *

UNITED STATES PATENT AND TRADEMARK OFFICE
CERTIFICATE OF CORRECTION

PATENT NO. : 5,516,943

DATED : May 14, 1996

INVENTOR(S) : Gao et al.

It is certified that error appears in the above-identified patent and that said Letters Patent is hereby corrected as shown below:

Col. 12: Claim 6, line 11, delete "2indanol" and insert therefor --2-indanol--.

Col. 14: Claim 18, line 10, delete "$R^1$ and $R^2$" and insert therefor --$R^1$ and $R^2$--.

Signed and Sealed this

Eighth Day of October, 1996

Attest:

BRUCE LEHMAN

Attesting Officer

Commissioner of Patents and Trademarks